US010737855B2

(12) United States Patent
Christensen et al.

(10) Patent No.: US 10,737,855 B2
(45) Date of Patent: Aug. 11, 2020

(54) CLOSURE FOR A CONTAINER

(71) Applicants: METROHM AG, Herisau (CH); SIGMA-ALDRICH INTERNATIONAL GMBH, St. Gallen (CH)

(72) Inventors: Björn Christensen, Speicherschwendi (CH); Fabian Wahl, St. Gallen (CH); Michael Weber, St. Gallen (CH); Samuel Schindler, Zürich (CH); Lukas Wilhelm, Zürich (CH)

(73) Assignees: METROHM AG, Herisau (CH); SIGMA-ALDRICH INTERNATIONAL GMBH, St. Gallen (CH)

( * ) Notice: Subject to any disclaimer, the term of this patent is extended or adjusted under 35 U.S.C. 154(b) by 1009 days.

(21) Appl. No.: 14/781,696

(22) PCT Filed: Apr. 1, 2014

(86) PCT No.: PCT/EP2014/056491

§ 371 (c)(1),
(2) Date: Oct. 1, 2015

(87) PCT Pub. No.: WO2014/161831

PCT Pub. Date: Oct. 9, 2014

(65) Prior Publication Data

US 2016/0052683 A1 Feb. 25, 2016

(30) Foreign Application Priority Data

Apr. 3, 2013 (EP) .................................... 13162169

(51) Int. Cl.

| | |
|---|---|
| ***A61M 5/32*** | (2006.01) |
| ***B65D 51/16*** | (2006.01) |

(Continued)

(52) U.S. Cl.

CPC ...... *B65D 51/1683* (2013.01); *B01L 3/50825* (2013.01); *B01L 3/563* (2013.01);

(Continued)

(58) Field of Classification Search

CPC .............. B65D 51/1683; B65D 51/245; B01L 3/50825; B01L 3/563; B01L 2200/025;

(Continued)

(56) References Cited

U.S. PATENT DOCUMENTS

| | | | |
|---|---|---|---|
| 4,141,058 A | 2/1979 | Mizohata et al. | |
| 5,342,346 A * | 8/1994 | Honda .................. | A61J 1/2089 604/411 |
| 5,846,489 A | 12/1998 | Bienhaus et al. | |
| 2002/0193777 A1* | 12/2002 | Aneas .................. | A61J 1/2096 604/411 |

(Continued)

FOREIGN PATENT DOCUMENTS

| | | |
|---|---|---|
| EP | 0 676 643 A2 | 10/1995 |
| EP | 1 847 469 A2 | 10/2007 |
| EP | 2 526 920 A2 | 11/2012 |

OTHER PUBLICATIONS

International Search Report Corresponding to PCT/EP2014/056491 dated Oct. 9, 2014.

(Continued)

*Primary Examiner* — Andrew J Mensh

(74) *Attorney, Agent, or Firm* — David & Bujold PLLC; Michael J. Bujold

(57) ABSTRACT

A closure (1) for a container comprising a connecting element (2) for connection of the closure to a container, a sealing device (3) for sealing the access to a container content and an interface (4) to an adapter having a coupling receptacle (5). The closure (1) has a delivery position and a use position. In the use position, the sealing device (3) is open. In the delivery position, the sealing device (3) is sealed in a gas and liquid fight manner.

19 Claims, 12 Drawing Sheets

(51) Int. Cl.
*B01L 3/00* (2006.01)
*B65D 51/24* (2006.01)

(52) U.S. Cl.
CPC ...... *B65D 51/245* (2013.01); *B01L 2200/025* (2013.01); *B01L 2200/026* (2013.01); *B01L 2200/0689* (2013.01); *B01L 2200/141* (2013.01); *B01L 2300/022* (2013.01); *B01L 2300/048* (2013.01); *B01L 2300/0681* (2013.01)

(58) Field of Classification Search
CPC ....... B01L 2200/026; B01L 2200/0689; B01L 2200/141; B01L 2300/022; B01L 2300/048; B01L 2300/0681
USPC .......................................................... 604/414
See application file for complete search history.

(56) References Cited

U.S. PATENT DOCUMENTS

| | | | | |
|---|---|---|---|---|
| 2005/0106075 | A1* | 5/2005 | Kitazawa | B01L 3/0293 422/523 |
| 2010/0168712 | A1* | 7/2010 | Tuckwell | A61J 1/2096 604/406 |
| 2010/0245056 | A1 | 9/2010 | Braun et al. | |
| 2013/0018354 | A1 | 1/2013 | Sund et al. | |

OTHER PUBLICATIONS

Written Opinion Corresponding to PCT/EP2014/056491 dated Oct. 9, 2014.
European Office Action issued in corresponding European Patent Application No. 14 713 863.0 dated Mar. 16, 2017.

* cited by examiner

Section C-C

Section B-B

CLOSURE FOR A CONTAINER

The invention relates to a closure for a container, an adapter for a closure, an adapter system, a method for removing a fluid from a container, a display element for displaying a functional state, a sealing device, and also the use of an adapter and/or of a closure according to the preambles of the independent claims.

In particular within the scope of laboratory applications, process reliability and process quality are of essential importance with the use of a wide range of fluids. Furthermore, it is advantageous when the operating comfort for the user is increased, which likewise contributes to process reliability.

Previous closures of containers for fluids in the laboratory field allow a secure closing and opening of the container, however impurities may be created, for example by the inflow of air. Furthermore, the connection of a container to an apparatus that uses the fluid is often complicated to produce, thus making the handling more difficult.

The object of the present invention is therefore to avoid the disadvantages of the prior art and in particular to create a closure, an adapter, a method for removing a fluid from a container, a display element, a sealing device, and the use of an adapter and/or of a closure that allow an easy and secure removal of a fluid from a container and reduce the cost and the sources of error of a user.

The object is achieved by a closure for a container, said closure comprising a connection element for connecting the closure to a container and a sealing device for sealing the access to a container content. The closure also comprises an interlace to an adapter having a coupling receptacle, wherein the closure has a delivery position and a use position. In the delivery position the sealing device is closed, in a gas- and liquid-tight manner, wherein the sealing device is opened in a use position. Channels for feeding and discharging air through the sealing device can be closed. A container equipped with such a closure is closed outwardly substantially in a gas- and liquid-tight manner, as will be explained hereinafter in detail.

Here, the channels are preferably closed to the outside and to the inside, wherein the sealing device and the channels are preferably part of the closure.

It may be made possible for air to be conveyed through the channels in a closed and in an open state through a filter element. In the closed state, i.e. in the delivery position, a closed air circuit is formed here by the channels and the filter element and does not allow any contact with external air.

Furthermore, a closure of this type enables the contamination- and leakage-free transportation of a fluid in a container as well as the simple connection to an adapter, wherein the closure is opened at the same time as, or prior to the connection to an adapter.

The sealing device closes the channels, in particular preferably in the delivery position with closed seal.

Defined channels for feeding and discharging air allow a particularly reliable and contamination-free working environment. The air is preferably conveyed through a filter element before it comes into contact with the container content. Furthermore, the channels are preferably closed in a delivery position and are only opened in a use position.

The sealing device preferably comprises a sealing device as described hereinafter.

The delivery position of the closure comprises a closed seal and preferably a closure of air feed channels and air discharge channels.

In the use position the seal is opened and a fluid from a container can be removed through the closure. However, the fluid preferably does not come into direct contact with external air, as will be explained hereinafter.

The connection element may comprise a thread.

A thread enables the closure to be fastened in a simple and uncomplicated manner to a matching mating thread of a container. Furthermore, bayonet closures or snap-fit closures are of course also possible.

The closure may comprise a cover element for opening and closing the closure, wherein the cover element preferably can be secured by means of a rupture element, which indicates first-time opening.

A cover element of this type enables the closure to be closed and reopened following the opening of the sealing device in a use position. A further rupture element on the cover element for indicating first-time opening makes the closure secure against manipulation.

The closure may comprise a filter element, through which, in particular in the use position, external air can be conveyed from outside, through the closure, into a container.

In order to be able to remove fluid from the container, an air feed is advantageous in order to enable a pressure compensation. The use of a filter element prevents the contamination of the content of the container by direct external air and thus enables work to be performed accurately and with a high level of quality.

Filter elements are preferably equipped with a material that is suitable for removing components from the ambient air that may cause a change to the container content. Here, the respective material is coordinated to the respective container content by routine measures that are conventional in the art. Typical examples of suitable materials include soda lime (a mixture of calcium hydroxide $Ca(OH)_2$ and sodium hydroxide NaOH; or also a mixture of potassium hydroxide KOH and barium hydroxide $Ba(OH)_2$); particle filters; molecular sieves, and silica gel.

The filter element may be detachable. The filter element is preferably detachable in a use position. The filter element may thus be exchanged and adapted to the respective situation.

The channels for feeding and discharging air in the closure may be formed, at least on a connection side to the filter element, particularly preferably as female Luer fittings (with an inner cone) or may be provided with a thread. In the case of a removable filter element, a tube for feeding inert gas thus can be attached particularly easily to the closure for example, even without connected filter element.

The filter element may also be removable and preferably exchangeable.

A selection of the filter medium is thus possible, and the closure can be used in a very versatile manner.

Furthermore, the filter element may comprise a filter path, which enables a chemical reaction of the filter material with the air flowing through the filter material. Here, a filter path is defined within the scope of the application as a distance between the air inlet into the filter element and air outlet from the filter element.

The closure may comprise a fixing element, which fixes the closure in a delivery position, wherein the fixing element is detachable. The fixing element is in particular preferably detachable in a destructible manner, and the closure can be brought into a use position following the detachment and preferably removal of the fixing element.

A fixing element of this type prevents the closure from reaching the use position prematurely if this is not yet desired. Furthermore, a fixing element of this type constitutes a visual indication of the opening state and/or of the delivery or use position of the closure. Fault-free working is therefore enabled in a simple manner.

The closure may comprise a data carrier, preferably a data carrier with destructible data transfer element, in particular preferably an RFID chip.

A data carrier enables the automatic identification of the closure and also of the data stored on the data carrier, such as data concerning the associated container and also the content of the container. This leads to a secure working environment, since important data can be transferred. By way of example, the content of the container can thus be identified in a fault-free manner. Furthermore, data such as volume, shelf life data or removed quantities can be determined via the data carrier and/or stored thereon. This leads to high-quality results. The data carrier may be optical and/or electronic.

The coupling receptacle may be movable along a longitudinal axis of the closure from a delivery position into a use position.

By means of a movability of the coupling receptacle, the use position with the coupling of a matching coupling element for the coupling receptacle can be achieved. The sealing device can be opened in particular independently of the use of the adapter, preferably by simply pressing down the closure, wherein a matching adapter is then attached fn a subsequent step.

The closure is preferably closed in a gas-tight and liquid-tight manner in a delivery position. In a use position fluid can be guided from the container through the closure. Nevertheless, the gas feed or air feed remains controlled by a filter element, such that no contamination can occur of the content of the container.

The sealing device may be opened, preferably broken, following removal of the fixing element and pressing down of the cover, wherein the closure can be fixed in the use position once the sealing device has been broken open.

The coupling receptacle thus remains in a use position once the seal has been broken open and can be identified by the user as already used. This increases the security and makes the use of the closure simple and reliable for the user.

In the use position the air purified in particular by a filter element can be conveyed through the closure.

The feed of air enables a pressure compensation and thus facilitates the removal of fluid from the container under contamination-free conditions.

The coupling receptacle may comprise engagement grooves, preferably eight engagement grooves. The provision of engagement grooves enables a coupling element to be inserted with an accurate fit and also enables an adapter to be aligned in a dedicated manner with the closure. Furthermore, the transfer of force from adapter to the closure is optimized. The engagement grooves preferably nave exclusively a guiding function for a coupling element of an adapter. In particular, the engagement grooves have no retaining function for fixing an adapter in a coupled state of closure and adapter. The engagement grooves exclusively prevent a rotational movement, but do not prevent a movement in or against the direction of insertion.

The sealing device may nave at least one predetermined breaking point, preferably exactly two predetermined breaking points, which preferably enables a simultaneous breaking open of the seal of the fluid in a container and of the seal of the channels for air feed and air discharge.

A particularly clean, reliable working environment is thus made possible, since the air channels also remain sealed initially, until they are required.

The closure may also comprise at least two seals. The closure preferably comprises a first seal for closing off the air channels with respect to external air in the use position, and a second seal for closing off the fluid to be removed at a removal device, such as a removal tube, in the use position.

The closure may comprise at least one fixing element, to which an adapter can be fastened, preferably can be fastened detachably.

A fixing element of this type may comprise an undercut or edge or retaining surface, which can be grasped by engagement elements of an adapter. An adapter is thus fixed and positioned securely on the closure.

The closure may be designed for multiple use and for this purpose in particular may not nave a delivery position different from the use position. A closure of this type may be designed such that it does not have a fixing element for fixing the closure in a delivery position.

A closure of this type can be easily connected to an adapter and can be used with different containers and/or adapters. This optimizes the costs in a laboratory.

The object is also achieved by a container, which is connected to a closure as described above and preferably is closed externally in a substantially gas-and liquid-tight manner.

A container of this type can be easily and securely connected to an adapter and enables secure storage and also contamination-free and easy removal of a fluid from the container.

The object is also achieved by an adapter for a closure, preferably a closure as described above, which comprises a connection point to an apparatus, preferably an evaluation unit and an interface to a closure. The interface also comprises a coupling element, which can be brought into engagement with a coupling receptacle of a closure, such that a fluid flow through the adapter can be produced, without direct contact between external air and fluid. The coupling element is movable relative to the adapter along the axis in a direction of insertion of the adapter into a closure.

An adapter of this type enables a secure and simple connection of a closure to an adapter in order to remove a fluid securely and easily from a container.

The adapter preferably has exclusively an effective channel for a medium from a container, preferably in the interior of the coupling element. The media thus remains contamination-free over its path through the adapter.

Within the scope of the invention an effective channel means that a quantity of fluid can flow through the channel in one direction, even if further subdivision elements are located in the channel.

An adapter of this type enables the contamination-free and simple removal of a fluid from a container and the continued conveyance of this fluid into an apparatus which requires the fluid. The work required for a user is simplified and reduced, and process reliability rises.

The coupling element may comprise engagement elements, preferably eight engagement elements, which can be inserted into engagement grooves of a coupling receptacle of a closure, as will be explained in greater detail hereinafter on the basis of exemplary embodiments. The engagement grooves are preferably arranged on a region of the coupling receptacle tapering conically in the direction of a container.

The provision of engagement elements allows the coupling element to be inserted in an accurately fitting, accurately oriented, simple and secure manner into the coupling receptacle of a closure, and therefore enables a secure connection of adapter and closure.

The engagement grooves of a coupling receptacle of a closure are particularly preferably arranged in a region of this coupling receptacle tapering conically in the direction of the container. These engagement grooves particularly preferably taper off in a flat manner in the further part of the region tapering conically in the direction of the container. It has been found that a particularly advantageous compromise between simple handling and functional reliability can be ensured as a result.

The coupling element may be movable relative to the adapter, preferably movable along the axis of a direction of insertion of the adapter into a closure.

A movable coupling element enables the accurately fitting connection between coupling element and coupling receptacle, independently of the fastening of the adapter to the closure. Furthermore, a reliable seal between the coupling element and a fluid removal tube of the closure is enabled by surface pressure. The fluid removal tube is formed here in a protruding manner, such that the coupling element comes to rest on the collar. It is therefore possible to dispense in a particularly advantageous manner with an additional sealing element.

The adapter may comprise lever elements, by means of which the coupling element can be moved relative to the adapter. The use of lever elements defines the movability of the coupling element relative to the adapter and thus enables an accurately fitting connection of adapter and closure.

The adapter may comprise fastening elements that can be brought into engagement with a fixing element of a closure, wherein the fastening elements are preferably mechanically detachable. The fastening elements particularly preferably are detachable during the movement of the coupling element.

The fastening elements enable an accurately fitting fixation of the adapter on a closure and a detachment. The fastening elements are preferably snap elements, which engage with an undercut of a closure. The adapter is thus securely connected to the closure.

The connection point may comprise a threaded coupling.

A threaded coupling enables a quick and secure connection of the adapter to an apparatus that requires fluid from a container comprising a closure.

The adapter may comprise a readout element for data, preferably readout electronics for an RFID chip.

By means of a readout element on the adapter, the adapter can read out data concerning the closure and therefore, if stored, also data concerning the container and concerning the fluid located in the container. This leads to greater process reliability, since errors caused by the user are eliminated.

The readout element may have a writing function for data. A writing function of this type enables the characterization of the closure and therefore also of the container by the adapter, such that for example the date of use, moments of coupling and decoupling of the closure or opening or consumption of fluid can be recorded.

This leads to increased process reliability.

The adapter may have a display element. In particular, the adapter may have a display element as described hereinafter. A display element of this type enables the display of a connection of adapter and closure.

The object is achieved by an adapter system for a container, which comprises a closure and also an adapter as described above.

The object is also achieved by a method for removing a fluid from a container, wherein the fluid is guided through an adapter system as described above.

A method of this type enables the secure and reliable removal of fluid from a container under contamination-free conditions.

The object is also achieved by a display element for displaying a functional state, in particular a coupling state between a closure as described above and an adapter as described above. The display element comprises at least one display body and also at least one light coupling-in device for coupling light into the display body. Light-deflecting elements for distributing the coupled-in light in the display body are also provided and distribute the coupled-in light in the display body.

A display element of this type displays clearly and reliably the coupling state between closure and adapter and thus leads to increased application security of adapter and closure.

The light-deflecting elements may comprise boundary surfaces.

Due to the use of boundary surfaces, the light is refracted and thus deflected. Furthermore, boundary surfaces can be produced easily and conveniently. The light is thus guided through the entire display body, and the display can thus be seen very clearly and easily.

Boundary surfaces within the scope of the application are surfaces at which the refractive index changes. Alternatively, other or additional reflective and/or diffractive elements may of course also be used.

The display body may comprise an upper side and an opposite underside, wherein the upper side is circular and the underside is arranged at an angle to the upper side from approximately 8° to approximately 20°, preferably from approximately 10° to approximately 15°, particularly preferably of approximately 12°.

A design of this type of the display body improves the distribution of light in the display body, in particular in the complete three-dimensional geometry of the display body, such that the display is visible from ail directions.

The object is also achieved by a sealing device for scaling a container, which scaling device comprises rupture elements for ultimately breaking open the seal by means of a break-open element for penetrating the rupture element in a direction of penetration. Furthermore, the sealing device comprises a fluid connection element for producing a connection to a fluid once the seal has been broken open. At least part of the rupture element is displaceable along the direction of penetration from a delivery position into a use position, wherein the rupture element preferably has a predetermined breaking point in the delivery position.

The predetermined breaking point is preferably arranged on the circumference of the rupture element, such that, once the predetermined breaking point has been broken open, the rupture element has a shorter vertical extent than in the delivery state. The force for breaking the predetermined breaking point preferably can be applied manually, for example in a range from 15 N to 30 N, preferably approximately 17 N to 25 N, particularly preferably approximately 20 N. In particularly preferred embodiments an even greater pressure leads to a perceptible snapping-in; the pressure to be applied for this purpose should lie approximately in a range from 30 N to 50 N, preferably approximately 35 N to 45 N, particularly preferably approximately 40 N. The handling is further improved as a result of this haptic feedback.

A design of this type of the sealing device enables a reliable display of the opening state and at the same time an optimal positioning of the fluid connection element for creating a fluid connection between fluid connection element and a coupling element.

The rupture element may comprise a first displaceable part and a second fixed part once the predetermined breaking point has been broken open. The first displaceable part is displaceable in a direction of penetration.

A complete rupture of the predetermined breaking point along the entire circumference is therefore clearly visible. This leads to improved process reliability, since the height of the sealing device along the entire circumference changes and can therefore be detected.

The rupture element may also have sealing flaps, which have predetermined breaking points between one another and are preferably each triangular.

The presence of sealing flaps enables the ultimate access to the interior of the sealing device and thus enables a gas- and liquid-tight design of the sealing device in a delivery position, and also, in a use position, easy insertion of a coupling element for removal of a fluid from a container.

Within the scope of the invention a triangular design of the sealing flaps means that the sealing flaps have at least three corners. Here, it is possible that the chords of the triangle are rounded, straight, or elliptical.

An adapter sis described above and/or a closure as described above can be used to pass through a fluid as said fluid is removed from a container.

The object is also achieved by a closure for a container, said closure comprising a connection element for connecting the closure to a container and comprising an interface to an adapter having a coupling receptacle. The closure also comprises a filter element, through which external air from outside can be conveyed through the closure into a container, wherein the filter element forms a filter volume that can be filled with filter material.

In order to be able to remove fluid from the container, an air feed is advantageous in order to enable a pressure compensation. The use of a filter element prevents the contamination of the content of the container by direct external air and thus enables work to be performed accurately and with a high level of quality.

Filter elements are preferably equipped with a material that is suitable for removing components from the ambient air that may cause a change to the container content. Here, the respective material is coordinated to the respective container content by routine measures that are conventional in the art. Typical examples of suitable materials include soda lime (a mixture of calcium hydroxide $Ca(OH)_2$ and sodium hydroxide NaOH; or also a mixture of potassium hydroxide KOH and barium hydroxide $Ba(OH)_2$); particle filters; molecular sieves, and silica gel.

The filter element may be detachable. The filter element is preferably detachable in a use position. The filter element may thus be exchanged and adapted to the respective situation.

The channels for feeding and discharging air in the closure may be formed, at least on a connection side to the filter element, particularly preferably as female Luer fittings (with an inner cone) or may be provided with a thread. In the case of a removable filter element, a tube for feeding inert gas thus can be attached particularly easily to the closure for example, even without connected filter element.

The filter element may also be removable and preferably exchangeable.

A selection of the filter medium is thus possible, and the closure can be used in a very versatile manner.

Furthermore, the filter element may comprise a filter path, which enables a chemical reaction of the filter material with the air flowing through the filter material. Here, a fitter path is defined within the scope of the application as a distance between the air inlet into the filter element and air outlet from the filter element. The necessary filter path differs depending on the filter material.

The closure may comprise a data carrier, preferably an RFID chip.

A data carrier enables the automatic identification of the closure and also of the data stored on the data carrier, such as data concerning the associated container and also the content of the container. This leads to a reliable working environment, since important data can be transferred. By way of example, the content of the container can thus be identified in a fault-free manner. Furthermore, data such as volume, shelf life data or removed quantities can be determined via the data carrier and/or stored thereon. This leads to high-quality results. The data carrier may be optical and/or electronic.

The closure may comprise at least one fixing element, to which an adapter can be fastened, preferably can be fastened detachably.

A fixing element of this type may comprise an undercut or edge or retaining surface, which can be grasped by engagement elements of an adapter. An adapter is thus fixed and positioned securely on the closure.

The invention will be explained in greater detail hereinafter in exemplary embodiments on the basis of figures, in which.

Figure 2:
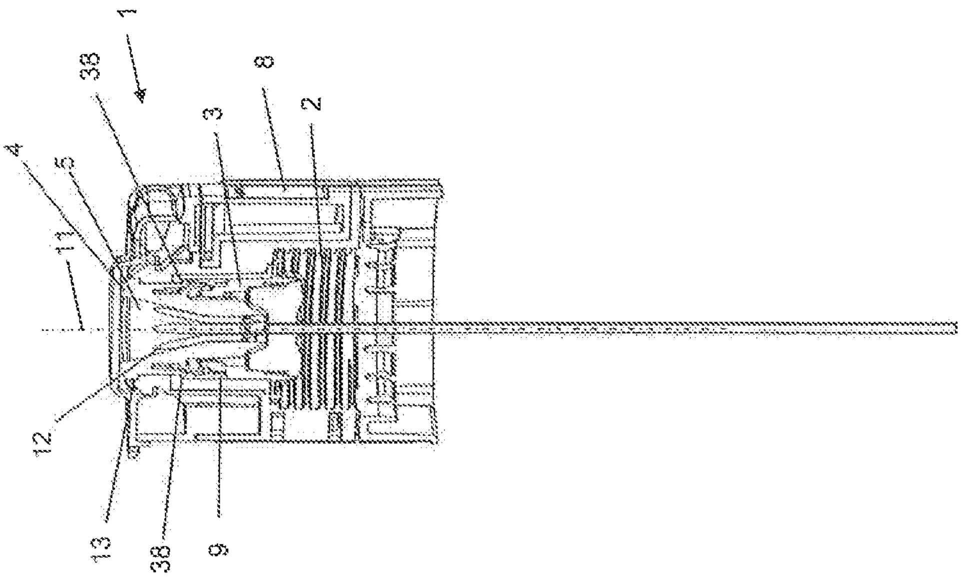
FIG. 2 shows a section through a closure according to the invention in a use position
Figure 6:
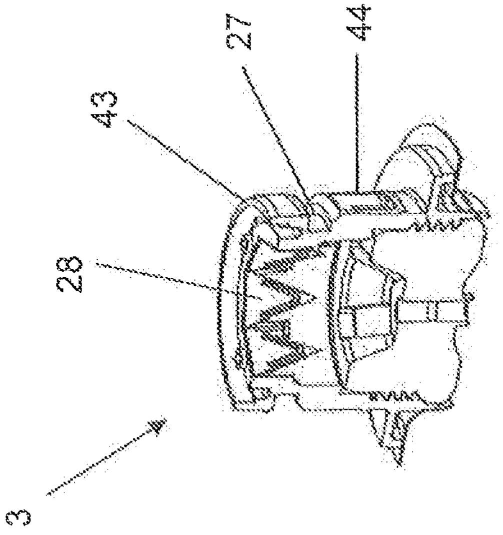
Figure 5:
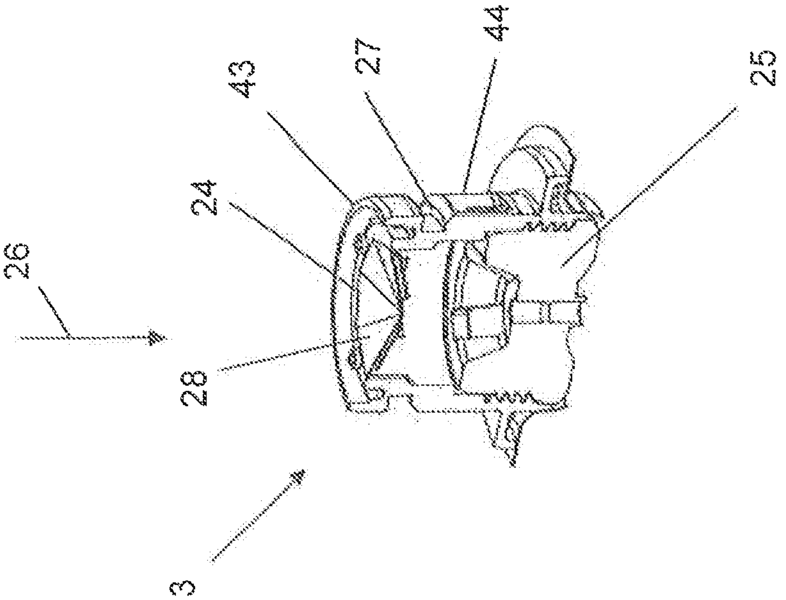
FIG. 5 shows a section through a sealing device according to tire invention
Figure 8:
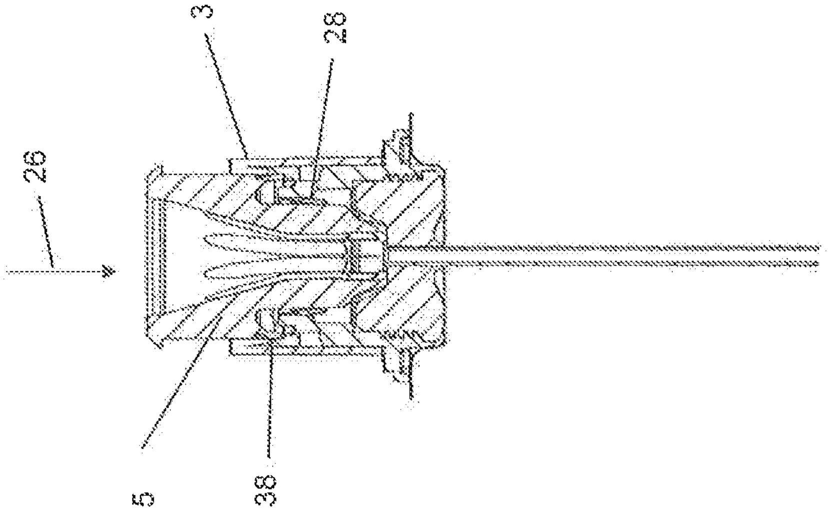
Figure 7:
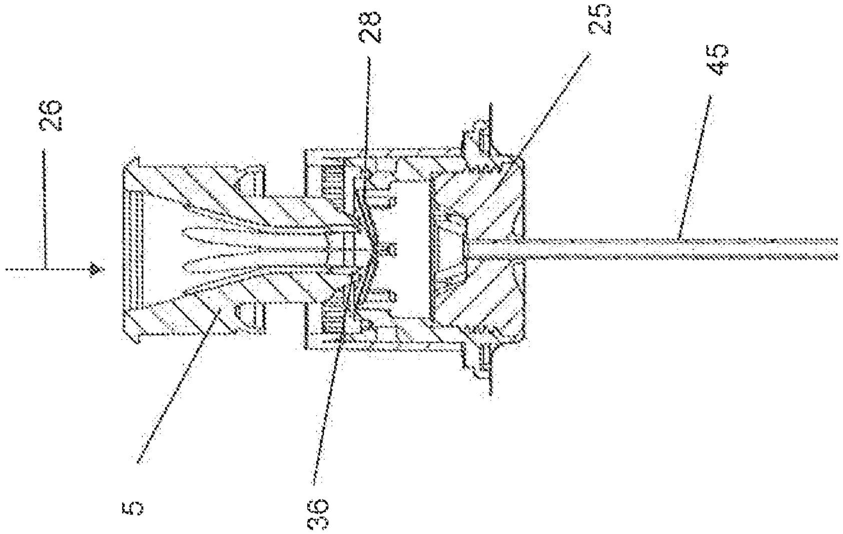
Figure 9:
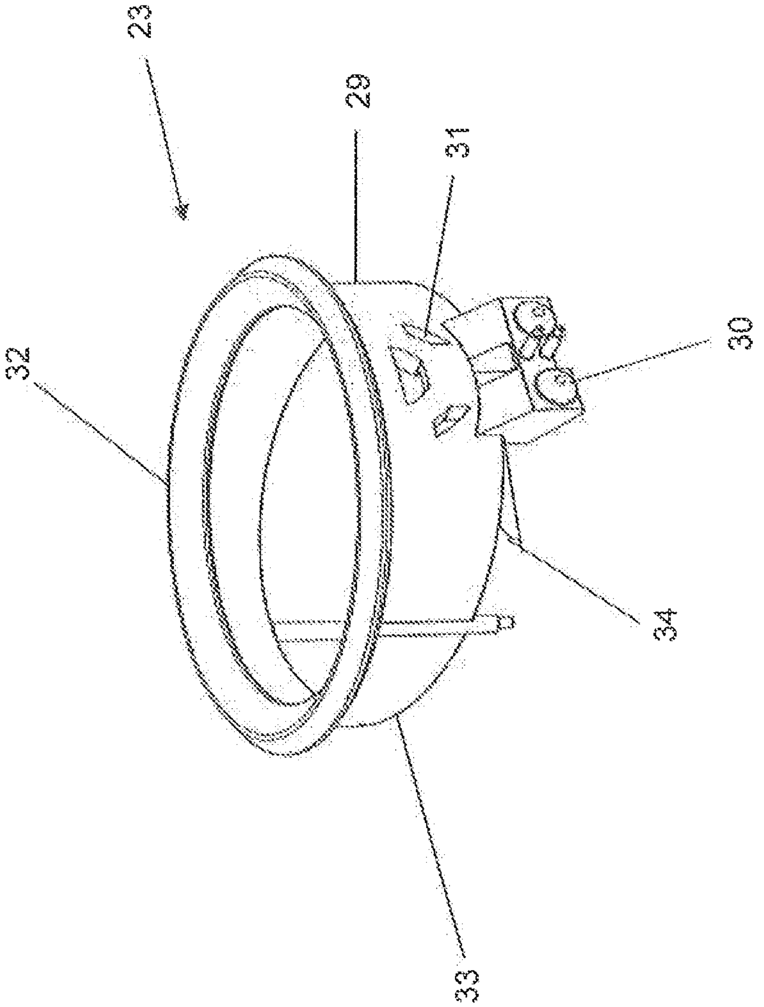
Figure 10:
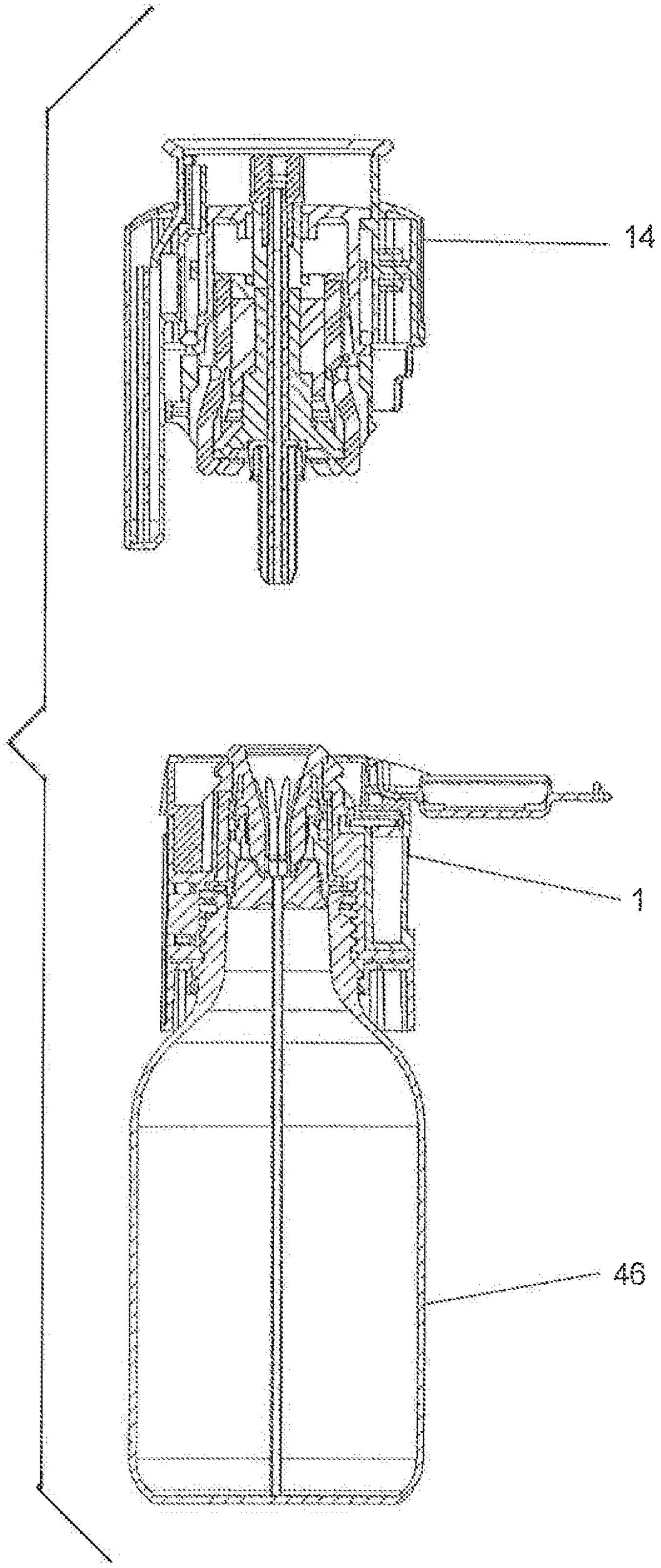
Figure 11:
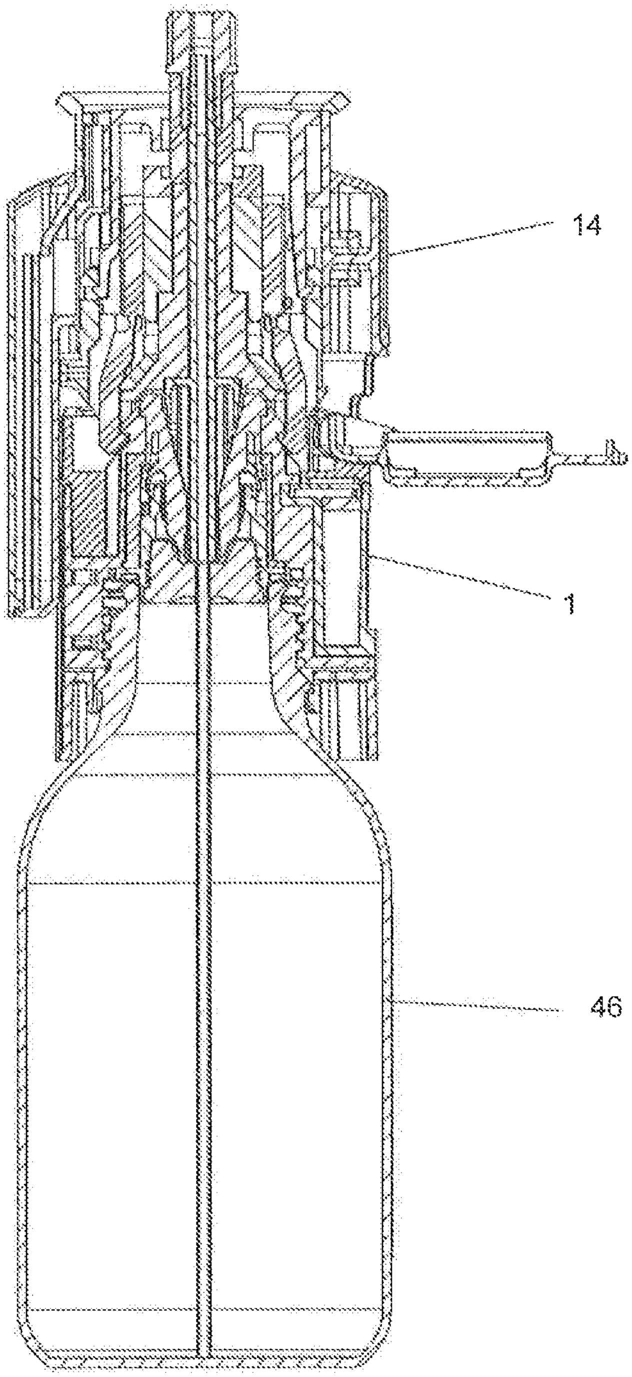
Figure 12:
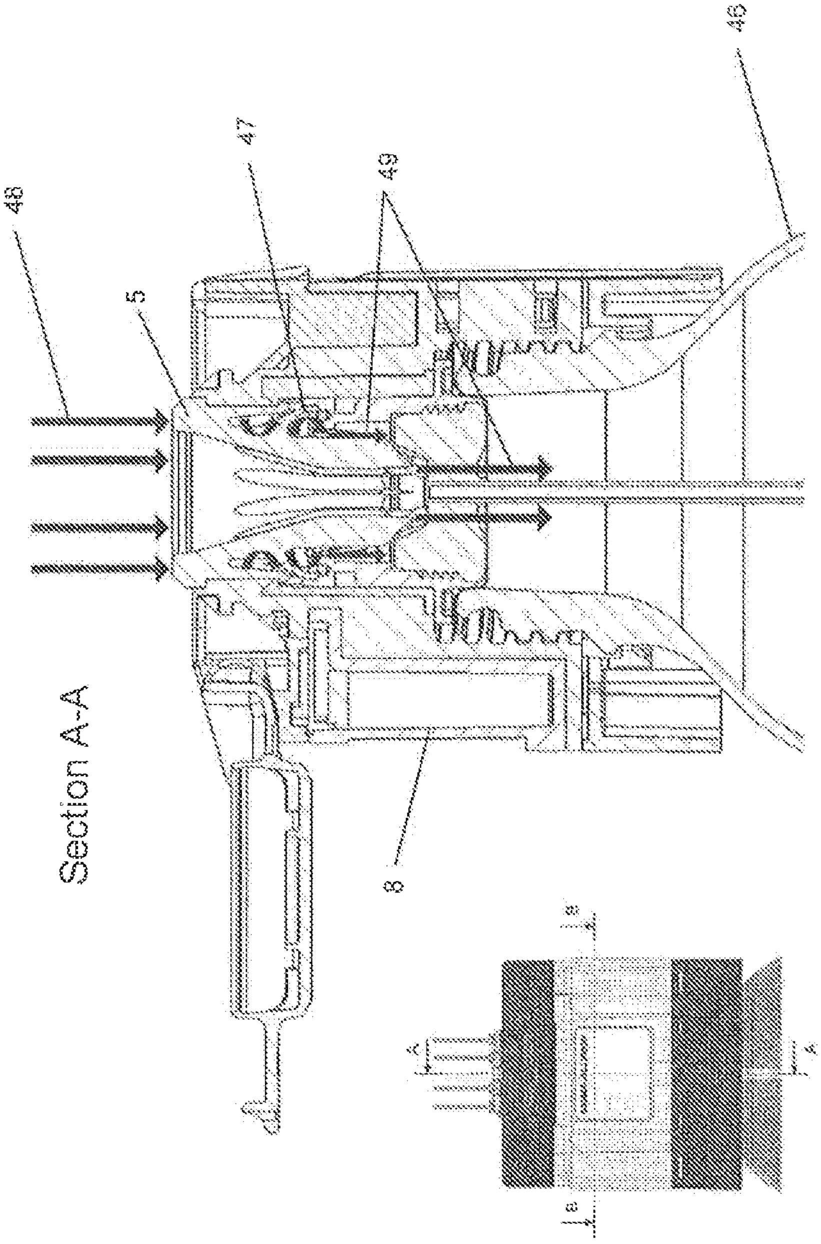
Figure 13:
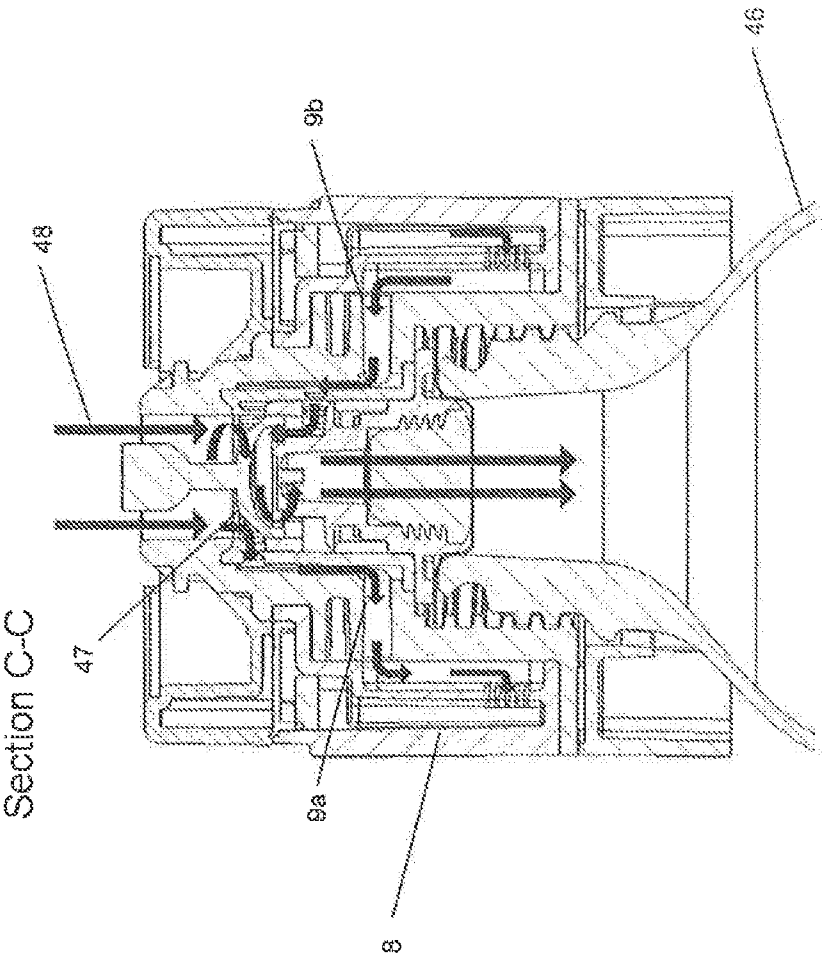
Figure 14:
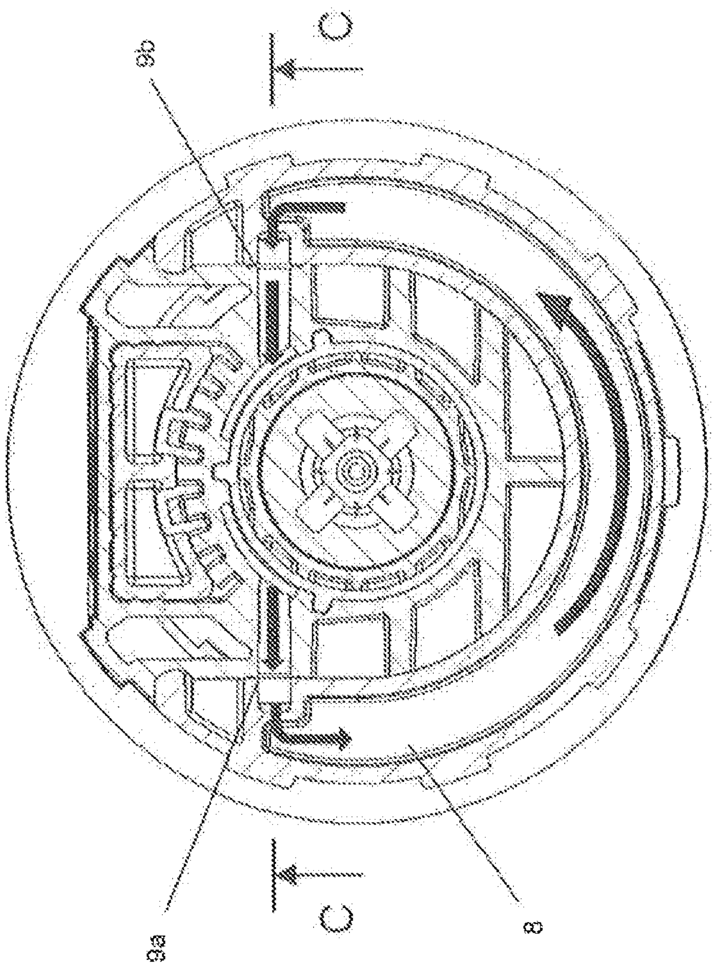

FIG. 6 shows a section through the sealing device from FIG. 5 with opened sealing flaps FIG. 7 shows a section through a sealing device according to FIG. 5 with a penetration element in a delivery position FIG. 8 shows a section through a sealing device according to FIG. 7 in a use position FIG. 9 shows a view of a display element FIG. 10 shows a sectional illustration through a closure with a container in use position and a decoupled adapter FIG. 11 shows a sectional illustration through a closure with a container in use position and coupled adapter FIG. 12 shows a sectional illustration through the middle of a closure according to FIG. 2 with designation of the air feed FIG. 13 shows a sectional illustration through a closure according to FIG. 12 through a second interface (see FIG. 14)

FIG. 14 shows a horizontal sectional illustration of a closure according to FIG. 2 with illustration of the plane of section from FIG. 13.

Figure 1:
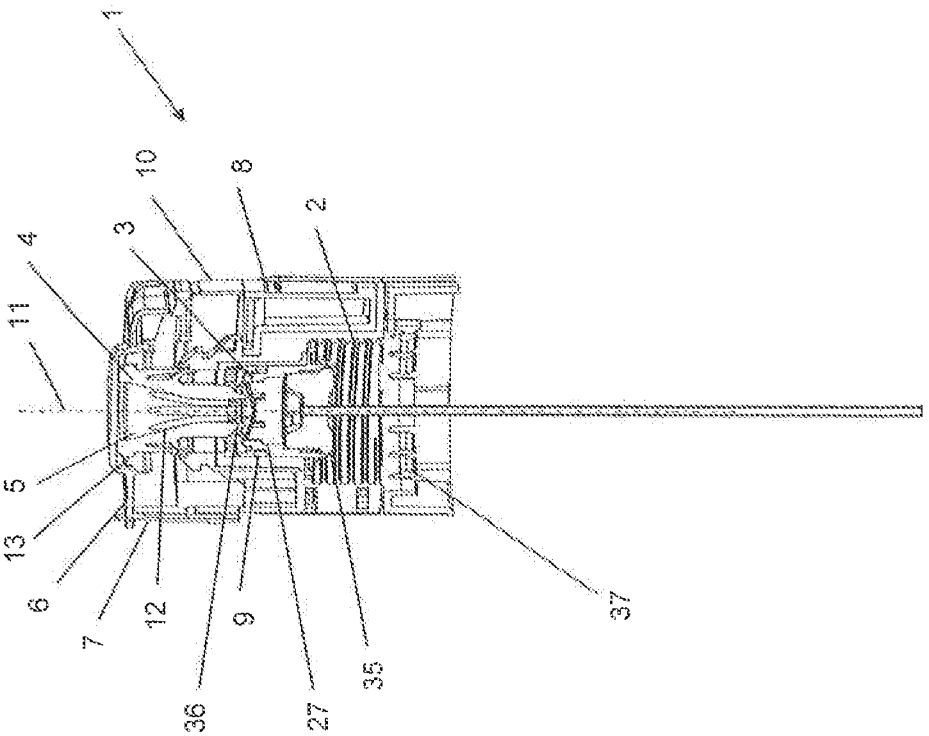
FIG. 1 shows a section through a closure according to the invention in a delivery position

FIG. 1 shows a section through a closure 1 according to the invention in a delivery position. The closure 1 comprises a connection element 2 to a container. The connection element 2 is formed by a thread which can engage with a matching mating thread of a container. Furthermore, the closure 1 comprises a sealing device 3, which seals the access to the interior of the container prior to first-time use.

The closure 1 also comprises an interface 4, which can be connected to an adapter. The interface 4 comprises a coupling receptacle 5, with which a coupling element of an adapter can engage. The coupling receptacle 5 at the same time constitutes a breakthrough element for breaking through the seal of the sealing device 3. The coupling receptacle 5 is displaceable along a longitudinal axis 11 in the direction of the container and thus pierces the sealing device 3 and breaks open the seal. At the same time, the sealing device 3 may comprise a further predetermined breaking point (see FIGS. 5 and 6). The coupling receptacle 5 also comprises eight engagement grooves 12, with which a matching coupling element having eight or fewer engagement elements can engage. A connection of this type enables an accurately fitting and accurately oriented connection, with reduced play, between an adapter and a closure 1. The interface 4 also comprises fixing elements 13 for an adapter. A seal element 35 is arranged below the sealing device 3, in a contact region between container upper edge and sealing device 3, and is formed by a PTFE film ring. The interface 4 also comprises perforation aids 36, which are aligned with predetermined breaking points of the sealing device 3. The closure 1 additionally comprises a cover element 6, which is fastened in a hinged manner on the closure. The closure 1 also comprises a rupture element 7, which indicates first-time opening of the cover. Furthermore, the cover element 6 is removable. By means of a cover element 6 of this type, the closure 1 can also be re-closed once the sealing device 3 has been opened. The closure 1 also comprises a fixing element 10 for the cover element, which fixes the interface 4 prior to use. Following the removal of the fixing element 10, which is removed by being torn off from the closure, the coupling receptacle 5 can be moved along the longitudinal axis 11, and the sealing device 3 can thus be broken open. Besides the sealing of the sealing device 3, which is broken open by the perforation aids 36 of the coupling receptacle 5, the sealing device 3 comprises a further predetermined breaking point 27, which is arranged on the circumference of the sealing device 3. By breaking open this predetermined breaking point 27, a first part of the sealing device 3 is displaced in the direction of the container along the longitudinal axis 11. Channels 9 are opened as a result of this displacement, through which channels air can be fed into the container. The air that can be guided through channels 9 into the container is purified beforehand by a filter element 8. There is thus no direct contact between the content of the container and the external air.

FIG. 2 shows the closure 1 from FIG. 1 in a use position. In the use position the coupling receptacle 3 is lowered. The seal of the sealing device 3 is broken open, and access to the interior of a container is made possible, such that fluid can be conveyed through the closure. The channel 9 is likewise accessible, such that air that has been guided through the filter element 8 can infiltrate the container. The closure 1 also has snappers 37, which fix the closure once screwed onto a container. The closure thus can be removed from the container only with difficulty or even cannot be removed at all. The closure 1 also has an interface 4, with a coupling receptacle 5, into which coupling elements of an adapter can be inserted. The fixing element 10 (see FIG. 1) is removed in the use position, and the closure 1 thus has a shorter height extent than in the delivery position. The coupling receptacle 5 has a region converging internally at least partially comically, such that a coupling element of an adapter can be easily inserted and centered. Furthermore, five snap elements 38 sere formed on the coupling receptacle and fix the coupling receptacle 5 in the use position; a different number of snap elements 38 is of course possible.

Figure 3:
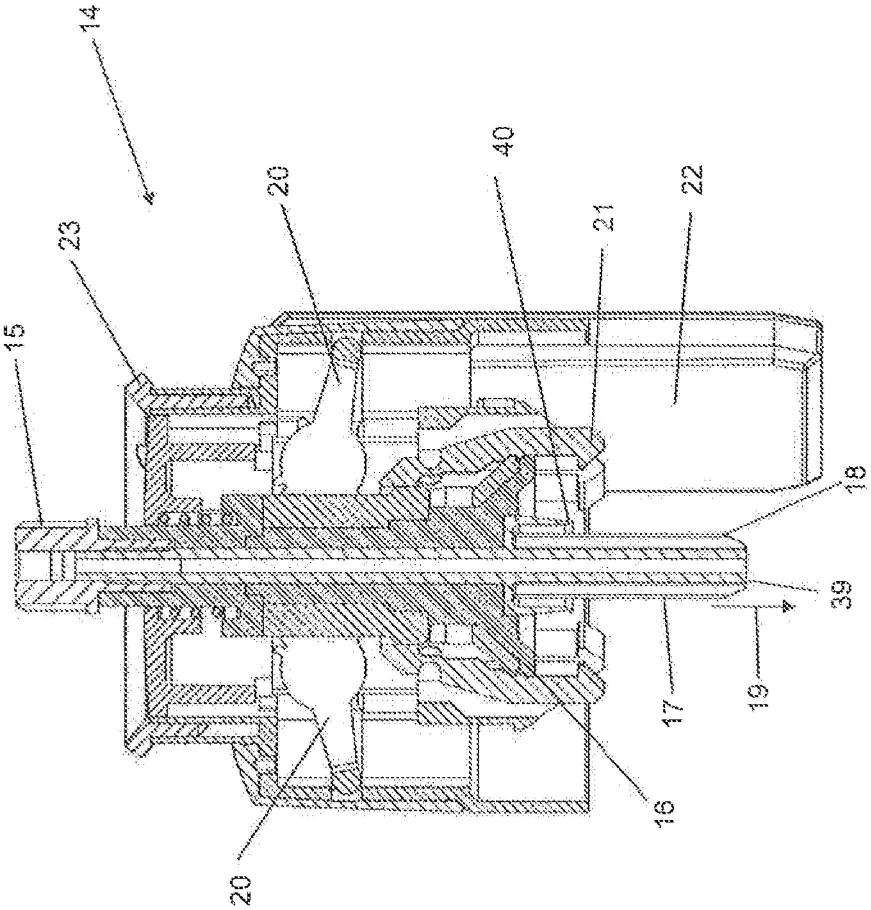
FIG. 3 shows a section through an adapter according to the invention in a coupled position (closure not shown)

FIG. 3 shows a section through an adapter 14 in the coupled state. The adapter 14 comprises an interface 16 to a closure and also a connection point 15 to an apparatus, such as an evaluation unit. The interface 16 to a closure (see FIGS. 1 and 2) comprises a coupling element 17, which has engagement elements 18 along its circumference. The engagement elements 18 can be Inserted into insertion grooves 12 (see FIG. 1) of a closure. The interface 16 is displaceable within the adapter 14 in the insertion direction 19. The coupling element 17 at its tip in the insertion direction 19 has a sealing face 39, which allows a removal of a fluid from a container via a closure 1 without leaks, losses or external contaminations. Furthermore, seal elements 40 are formed on the coupling element 17 and enable a hermetic air seal when the adapter 14 is connected to a closure. The extent of the movement of the coupling element 17 relative to the adapter 14 is delimited and controlled by lever elements 20. The interface 16 to a closure also has fastening elements 21, which connect the adapter 14 detachably to a closure 1 (see FIG. 1 or 2). The adapter 14 also has a readout element 22 for data of a closure 1 (see FIG. 1 or 2). The readout element may preferably read out RFID data. Data of a closure can thus be forwarded directly via the adapter 14 to an apparatus. The adapter 14 also has a display element 23 (see also FIG. 9), which indicates the connection of the adapter 14 to a closure. The display element 23 is therefore illuminated in the event of a successful connection. In the knowledge of the invention, it is clear that further states can also be Indicated (for example error messages; no RFID found; incorrect RFID found; crosstalk of a number of RFIDs; expiring shelf life in the coupled state; etc.).

Figure 4:
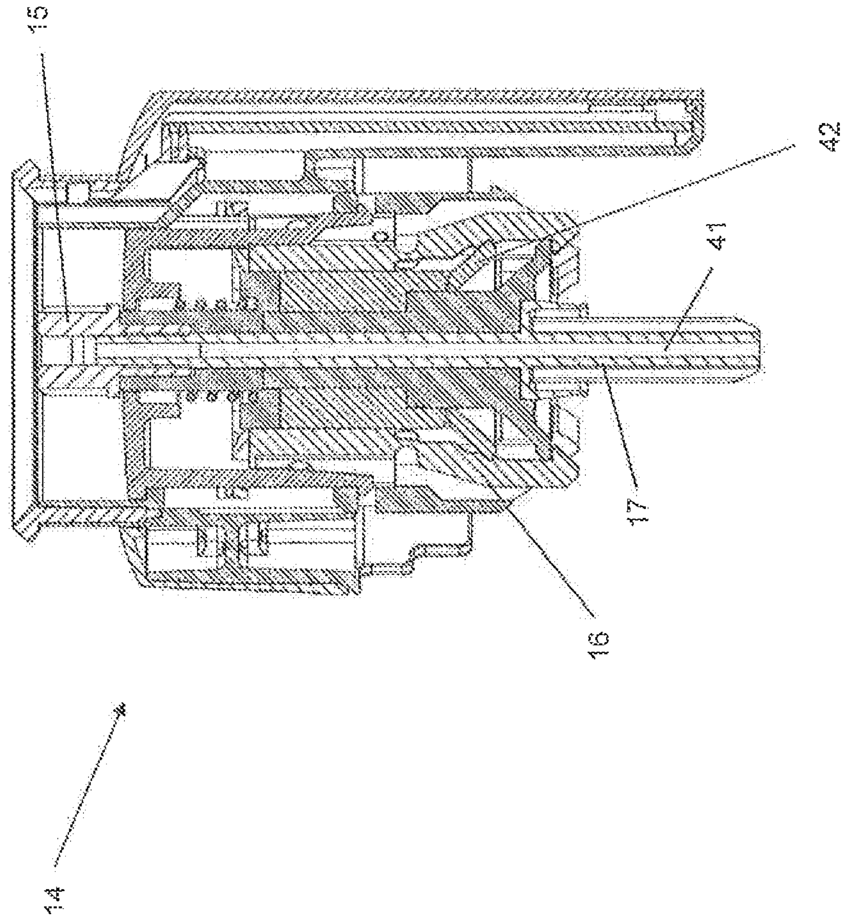
FIG. 4 shows a section through the adapter from FIG. 3 in a decoupled position (closure not shown)

FIG. 4 shows a section through an adapter 14 as in FIG. 3, but in the decoupled state. The adapter 14 is formed similarly to the description of FIG. 3. In the decoupled state, however, the interface 16 to a closure is lowered in the direction of the insertion direction 19. The interface 16 comprises a coupling element 17, which in the anterior has a tubular cavity 41 for conveying fluid. This cavity 41 extends as far as the connection point 15, such that the fluid can then be conveyed into an apparatus. The interface 16 also has a detent element 42. By actuation of the detent element 42 against the insertion direction 19, the fastening elements are splayed and the adapter 14 can be detached from the closure. The detent element is forced in the insertion direction 19 as the adapter 14 is detached from the closure. The adapter with the detent element is thus in the decoupled state again following the detachment.

FIG. 5 shows a section through a sealing device according to the invention in a sealed state. The sealing device 3 has a rupture element 24 and a fluid connection element 25. The rupture element 24 has sealing flaps 28, which can be broken through by means of a penetration element in a penetration direction 26. The sealing device 3 is also provided with a predetermined breaking point 27 arranged on the circumference. The predetermined breaking point 27 divides the rupture element 24 into a first part 43 and a second part 44. A predetermined breaking point of this type may be provided, but is not absolutely necessary.

FIG. 6 shows the sealing device 3 from FIG. 5 with broken-open sealing flaps 28. The sealing flaps 28 are triangular and remain fixed to the sealing device 3 along the circumference of the opening. The predetermined breaking point 27 is not yet broken open at this stage. In order to achieve the complete use position, the predetermined breaking point 27 is also broken open along the circumference of the sealing device 3, and the first part 43 of the sealing device 3 is inserted partially into the second part 44 of the sealing device 3.

FIG. 7 shows a section through a sealing device 3 according to FIG. 5 with a penetration element in a delivery position. The penetration element is formed by the coupling receptacle 5 (see FIG. 1 or 2) and penetrates the sealing flaps 28 in the penetration direction 26. For this purpose, the coupling receptacle 5 has, at its front tip, perforation aids 36, which each fit accurately between two sealing flaps and thus break open the sealing flaps. In addition to the embodiment illustrated in FIG. 5, the fluid connection element 25 has a removal tube 45, which preferably reaches to the bottom of the container, in which the closure with the sealing device is arranged.

FIG. 8 shows the sealing device 3 with the coupling device 5 from FIG. 7 in a use position. The coupling receptacle 5 is displaced in the direction of the penetration direction 26 and has broken open the sealing flaps 28. The sealing flaps 28 remain fastened to the sealing device 3, but rest laterally against the coupling receptacle. The coupling receptacle 5 also has snap elements 38, which engage with undercuts in the sealing device 3, such that the coupling receptacle 5 remains fixed in its position.

FIG. 9 shows a display element 23, which displays the coupling state of an adapter 14 (see FIGS. 3 and 4) and a closure 1 (see FIGS. 1 and 2). The display element 23 has a display body 29 and a light-coupling device 30. The light coupled in, for example LED light, is directed by the light-coupling device 30 onto light-deflecting elements 31 and is distributed by the light-deflecting elements 31 in the display body 29. The light-deflecting elements 31 are cutouts in the display body 29 consisting of transparent polyethylene terephthalate (PET). Boundary surfaces are thus formed by the light-deflecting elements 31, and the light coupled in is reflected. The shapes of the light-deflecting elements 31 are such that the light is distributed as uniformly as possible in the display body 29. The light is thus deflected substantially by 90°, wherein the deflection surfaces are not straight, but are slightly curved. A broader scattering of the light within the display body 29 is thus achieved. The display body 29 has an upper side 32 and an underside 33. The underside 33 is inclined at an angle 31 to the upper side 32. The angle 34 is 12°. The display body 29 has a round shape and also a flange-like bulge on the upper side 32 in order to optimize visibility.

FIG. 10 shows a section through a closure with a container 16 in a use position and an adapter in the decoupled state. The adapter system consists of a closure 1 (see FIGS. 1 and 2) and an adapter 14 (see FIGS. 3 and 4).

FIG. 11 shows a section through an adapter system on a container 46 in a use position.

FIGS. 12, 13 and 14 show the closure from FIG. 2 in sectional illustrations with illustration of the air feed through the closure 1. External air is in each case diverted such that no external air can pass directly through the closure. FIG. 12 shows the external air 48, which can infiltrate the closure only as far as a seal element 47. From there, the external air 48 is conveyed through the filter element 8, which in particular represents an absorber element, such that only purified air 49 can infiltrate the container 46.

FIG. 13 shows a second interface (see FIG. 14 with regard to the position), by which the flow of air can be illustrated more accurately. The external air 48 is conveyed through seal elements 47 into a lateral channel 9 and from there into the filter element 8, which is arranged at least partially on the circumference of the closure 1. The air is filtered through the filter element and introduced into the channel 9*b*, through which the air is conveyed into the interior of the closure 1 into the container 46.

FIG. 14 shows a horizontal section through the closure 1 from FIG. 13. The air circuit passes through the channel 9*a* into the filter element 8 at the circumference of the closure 1, and through the channel 9*b* into the container 46 (see FIG. 13).

The invention claimed is:

1. A closure for a container comprising:

a connection element for connecting the closure to the container, a sealing device for sealing an access to a container content, and an interface to an adapter, wherein the interface to the adapter comprises a coupling receptacle, the closure has a delivery position and a use position, the sealing device is substantially closed in a gas and liquid tight manner in the delivery position, the sealing device is open in the use position, and channels for feeding and discharging air are configured to be closable by the sealing device, and the coupling receptacle is movable along a longitudinal axis of the closure from the delivery position into the use position by means of force transferred from the adapter to the closure, and the coupling receptacle comprises engagement grooves, wherein the engagement grooves exclusively have a guiding function for a coupling element of the adapter and wherein the engagement grooves are configured to prevent rotational movement between the adapter of the closure.

2. The closure according to claim 1, wherein a cover element for opening and closing the closure is formed on the closure.

3. The closure according to claim 1, wherein the closure comprises a filter element, configured such that through the filter element external air can be conveyed from outside, through the closure, into the container.

4. The closure according to claim 1, wherein the closure comprises a fixing element, which fixes the closure in the delivery position, the fixing element is detachable, and the closure is configured such that the closure can be brought into the use position following detachment of the fixing element.

5. The closure according to claim 1, wherein the closure comprises a data carrier.

6. The closure according to claim 1, wherein the sealing device is configured such that the sealing device can be broken by movement of the coupling receptacle, and the coupling receptacle can be fixed in the use position once the sealing device is broken.

7. The closure according to claim 1, wherein in the use position purified air can be conveyed through the closure.

8. The closure according to claim 1, wherein the sealing device has at least one predetermined breaking point.

9. The closure according to claim 8, wherein the closure comprises at least two seals.

10. A closure which is designed for multiple use and for this purpose does not have a delivery position different from a use position.

11. The container which is connected to the closure according to claim 1.

12. An adapter for the closure according to claim 1 further comprising a connection point to an apparatus and an interface to the closure, wherein the interface to the closure comprises a coupling element, which is configured to be brought into engagement with the coupling receptacle of the closure, such that a fluid flow through the adapter is generated without direct contact of external air and fluid, and the coupling element is configured to be moved, relative to the adapter, along an axis in an insertion direction of the adapter into the closure, and the coupling element comprises engagement elements which are configured to be inserted into the engagement grooves of the coupling receptacle of the closure.

13. The adapter according to claim 12, wherein the adapter comprises a readout element for data.

14. The adapter according to claim 12, wherein the adapter has a display element.

15. The closure according to claim 2, wherein the cover element is configured to be secured by a rupture element which indicates a first-time opening of the closure.

16. The closure according to claim 1, wherein the engagement grooves have no retaining function for fixing the adapter in a coupled state of closure and adapter.

17. The closure according to claim 9, wherein the closure comprises a seal for closing off the air channels with respect to external air and a second seal for closing off the fluid to be removed at a removal tube.

18. The closure according to claim 10, wherein the closure also does not have a fixing element.

19. The closure according to claim 1, wherein the engagement grooves are arranged on a region of the coupling receptacle which taper conically in a direction of the container.

* * * * *